United States Patent [19]

Schasfoort et al.

[11] Patent Number: 5,545,303
[45] Date of Patent: Aug. 13, 1996

[54] SYSTEM FOR ANALYZING THE CONCENTRATION OF A NUMBER OF DIFFERENT IONS IN A WATERY SOLUTION

[75] Inventors: Richardus B. M. Schasfoort, Amersfoort; Jan O. Voogt, Maasdijk, both of Netherlands

[73] Assignee: Innocom (I.T.) B.V., 'S-Gravenzande, Netherlands

[21] Appl. No.: 214,293

[22] Filed: Mar. 17, 1994

[30] Foreign Application Priority Data

Mar. 17, 1993 [NL] Netherlands .......................... 9300475

[51] Int. Cl.$^6$ .......................... G01N 27/26; G01N 27/447
[52] U.S. Cl. .......................... 204/601; 204/602; 204/603; 204/604; 204/451
[58] Field of Search .......................... 204/180.1, 299 R, 204/601, 602, 603, 604, 451, 452, 453

[56] References Cited

U.S. PATENT DOCUMENTS 5,223,114  6/1993  Zare et al. .......................... 204/299 R
5,298,139  3/1994  Huang et al. .......................... 204/299 R

FOREIGN PATENT DOCUMENTS 9002723  7/1991  Netherlands .

OTHER PUBLICATIONS

By X. Huang et al., "On–Column Conductivity Detector for Capillary Zone Electrophoresis", Analytical Chemistry, Dec. 1, 1987, vol. 59, No. 23, pp. 2747–2749.

"Capillary Zone Electrophoresis with Electrochemical Detection in 12.7 μm Diameter Columns", Analytical Chemistry, Sep. 15, 1988, vol. 60, No. 18, pp. 1972–1975.

*Primary Examiner*—Arun S. Phasge
*Attorney, Agent, or Firm*—Young & Thompson

[57] ABSTRACT

System for analyzing the concentration of a number of different ions in a watery solution, using a capillary zone electrophoresis apparatus comprising a capillary tube extending between an input opening and a detection area and filled with an electrolyte, an input device for injecting a sample of the solution to be analyzed in the input opening of the capillary tube, a voltage source for establishing a voltage gradient along the capillary tube between the input opening and the detection area to evoke a migration of the ions in the same through the capillary tube, and a detector circuit for detecting the ions passing through the capillary tube by measuring the conductivity of the passing fluid. The system comprises furthermore a processor for calculating the ion concentrations, the processor receiving data from the detector circuit and from a further conductivity sensor providing to the processor data representing the total conductivity of the solution from which the sample was taken. By comparing the data from both detectors the calculated ion concentrations can be calibrated.

13 Claims, 4 Drawing Sheets

SYSTEM FOR ANALYZING THE CONCENTRATION OF A NUMBER OF DIFFERENT IONS IN A WATERY SOLUTION

FIELD OF THE INVENTION

The invention relates to a system for analyzing the concentration of a number of different ions in a watery solution, using a capillary zone electrophoresis apparatus comprising a capillary tube extending between an input opening and a detection area and filled with an electrolyte, an input device for injecting a sample of the solution to be analyzed in the input opening of the capillary tube, a voltage source for establishing a voltage gradient along the capillary tube between the input opening and the detection area to evoke a migration of the ions in said sample through the capillary tube, and a detector circuit for detecting the ions passing through the detection area by measuring the conductivity of the passing fluid.

BACKGROUND OF THE INVENTION

Systems of this kind are known from various prior art publications. Typical examples are described in the European patent application EP-0,295,942 and the U.S. Pat. No. 3,932,264.

During operation a sample of the solution to be analyzed is injected by the input device into the input opening of the capillary tube. In the following migration process the voltage source is switched on to start the migration in the capillary tube in the course of which each ion will start to move according to its own mobility through the capillary tube. Because of the mobility differences the ions in the electrolyte will be separated into zones such that ions of different type will pass the detector at different times which are characteristic for the type of ions. The strength of the signal generated by the detector circuit as a zone of ions passes the detector is related to the concentration of the respective type of ions.

A problem in said prior art systems is the calibration of the system. If the length of the capillary tube between the input opening and the detector area is selected long enough, establishing a relatively long migration period, the separation between the various kinds of ions will be distinct enough to enable the identification of each ion type on the basis of the elapsed time period between the moment of sample injection and the moment the respective ions pass the detector area. Especially if the number of different types of ions is rather restricted the influence of variable parameters such as the electrolyte composition and the temperature thereof will be negligible and identification of the ion type will be rather straightforward and can be performed by a suitably programmed processor.

However, an accurate determination of the concentration of the ions of a specific type is not so easy. In the course of the migration through the capillary tube the ions are separated type by type in bands or zones which have a certain width, said width being proportional to the number of ions. Because of said width the signal generated by the detector circuit will gradually increase to a peak level and will from there decrease. Furthermore a "background" signal will be generated even if only the electrolyte without any injected ions is present in the detector area, the level of the background signal being dependent on the composition of the electrolyte. Further parameters influencing the generated signal are the temperature of the electrolyte in the capillary tube, and the degree of stabilization of the voltage supplied by the voltage source for developing the voltage gradient in the capillary tube.

Even if the influence of temperature and voltage stability is reduced to a negligible level still the calibration of the system is rather cumbersome and inaccurate, mainly based on comparison of the detector signals with signals received from standard samples containing well-known concentrations of a specific ion.

SUMMARY OF THE INVENTION

An object of the invention is now to provide a system of the type mentioned in the first paragraph of this specification, which system is embodied such that the system has an auto-calibration facility. In other words, the system should be embodied such that the processor receives sufficient information to enable the processor under control of suitable software to provide relatively accurate data about the various ion concentrations even if the above-mentioned parameters change.

In agreement with said object, the invention proposes a system of the type mentioned in the first paragraph which according to the invention is characterized in that the system comprises furthermore a processor receiving data from said detector circuit representing the momentary peak levels in the measured conductivity as well as the moments in time at which the respective peaks appear, and a further conductivity sensor providing to said processor data representing the total conductivity of the solution from which the sample was taken, said processor being programmed to determine for each detected peak in the measured conductivity level the kind of ion and the concentration of the respective ion based on the data received from said detector circuit, whereafter the total conductivity is calculated and is compared with the total conductivity data provided by said further conductivity sensor to calibrate the calculation parameters such that both the measured total conductivity and the calculated total conductivity will be equal.

A further disadvantage of the prior art systems is that basically all these systems are destined for one time operation whereby after each operation human assistance is necessary to evaluate the measurement signals, to clean the capillary tube and to inject another sample in the input opening of the capillary tube. If a system is used for one time analysis of a certain solution, for instance under laboratory conditions, the need for automating the system is not high.

However, if such a system is used under more industrial circumstances for the repeated analysis of a certain solution, such as the continuous analysis of sewage water, waste water from industrial processes or agricultural production environments, then there certainly is a need for highly automated systems. None of the prior art systems is suited to become integrated in an autonomously functioning measurement and/or control system.

A further object of the invention is therefore to embody the system such that the system is able to operate in a semi-continuous manner without human assistance.

In agreement with said object, the invention provides a system which is characterized in that the input device is embodied such that the input device comprises switching means for switching the input device between a first condition in which clean electrolyte is supplied to the input opening of the capillary tube and a second condition in which the solution to be analyzed is supplied to the input opening of the capillary tube, said switching means being connected to the processor to be controlled thereby.

As remarked above, the calibration problems with respect to the identification of the type of ions can be significantly reduced if the number of different types of ions is restricted, and especially if the ions will become separated in well distinguished zones with relatively long intermediate intervals. If it is known in advance which ions could be present in the solution then the problems relating to the identification of the various ion types will be practically reduced to zero. In many practical situations the majority of ions in the solution to be analyzed are identified in advance and the main question is in fact "what is the concentration of each ion type ?". Typical examples of such a practical situation are found in the chemical industry where sewage water flows have to be analyzed to maintain the ion concentration levels within prescribed limits and in the agriculture, where the composition of nutrient solutions should be maintained within prescribed margins.

A typical example of a system, which is specifically destined for the analysis of ion concentrations in a nutrient solution for agricultural purposes is described in the Dutch patent application NL 9002723. In this prior art system, the ion concentrations are measured by means of an analyzer which functions according to an ion electrode method. In other words, the ion concentrations are measured by means of ion-selective semiconductors, such as CHEMFET's. The disadvantage of such ion-selective semiconductors is that therewith per sensor only one specific ion from the solution can be detected. For a part of the ions, which at this moment are present in the average nutrient solution, there are no suitable sensors available.

Furthermore sensors with a long-time stability are at this moment technically not realizable. On the one hand because of technological problems during the manufacturing thereof, on the other hand because of the fact that such sensors are susceptible to chemical degeneration.

An other prior art system is described in the U.S. Pat. No. 4,992,942. Therein a multiple nutrient sensor is used, which according to the very short description may function according to an ion-chromatographical principle or can be embodied with chemically sensitive field effect transistors, such as the above-mentioned CHEMFET's. The use of an apparatus, by means of which ion concentrations in a fluid can be analyzed by ion chromatography requires, however, a large level of skill and experience.

In fact such apparatuses are only used in specialized firms or laboratories. In the present situation the grower sends samples of the nutrient solution, which is used in the culture of plants, to such a laboratory where the suitable apparatus is present and where the ion concentration analysis is performed. On the basis of the information, which is sent by the laboratory to the grower, the composition of the nutrient solution will be amended by adding water and/or nutrients. Because of the time consuming process and because of the costs involved, such an analysis is only performed once a week or with an even lower frequency, so that in general the grower has no recent information available.

The purpose of the invention is now to embody a system of the type mentioned in the first paragraph, such that the concentrations of all or practically all ions in the nutrient solution can be detected, for which purpose apparatuses are used:

which do not require specific skill for the operation thereof, supplying signals which can be relatively easy delivered to the measurement and control installations which are common in horticulture, which provide with a much higher frequency than usual at present information about the nutrient solution, for instance once per hour, so that this information can be used in an online control and/or watch system, which are functioning reliable and stable of a long time period, which are based on a known proven measuring principle, which can be calibrated easily and automatically.

To fulfil at least part of the above-mentioned objects the invention relates specifically to a system for growing plants, which system comprises:

means for supplying a nutrient solution to a culture of plants, means for receiving drain water derived from the culture of plants, reservoirs containing the separate nutrients, a source of clean water, mixing means for mixing controlled amounts of drain water, clean water and one or more separate nutrients to prepare a nutrient solution, an analyzing apparatus for analyzing the ion concentrations of the dissolved nutrients, and a controller receiving signals from said analyzing apparatus and controlling the mixing means such that a nutrient solution of the desired composition is obtained, which system is characterized in that the ion concentrations are measured by means of an ion detector functioning with capillary zone electrophoresis.

Preferably, as already indicated, the concentrations are determined by means of a conductivity measurement.

It is indicated above that as such measurements are known in which capillary zone electrophoresis is used, for instance from the European patent application EP 0295942 and the U.S. Pat. No. 3,932,264. The application of such apparatuses within a system for controlling the ion concentration in a nutrient solution, used for growing plants is, however, not even suggested.

In a preferred embodiment the system according to the invention is characterized in that the system comprises two capillary tubes, a first one for the positive ions and a second one for the negative ions, each connected to said input device and each extending between said input device and a respective first and second detection area, whereby a first detection circuit is installed in the first detection area to detect the passage of the positive ions and a second detection circuit is installed in the second detection area to detect the passage of the negative ions, both detector circuits being connected to said processor to simultaneously supply measurement signals, and whereby the voltage source is embodied to develop a voltage gradient of the one polarity in the first capillary tube and a voltage gradient of the other polarity in the second capillary tube.

BRIEF DESCRIPTION OF THE DRAWINGS

The invention will be explained in more detail with reference to the attached drawings.

DETAILED DESCRIPTION OF THE INVENTION

Figure 1:
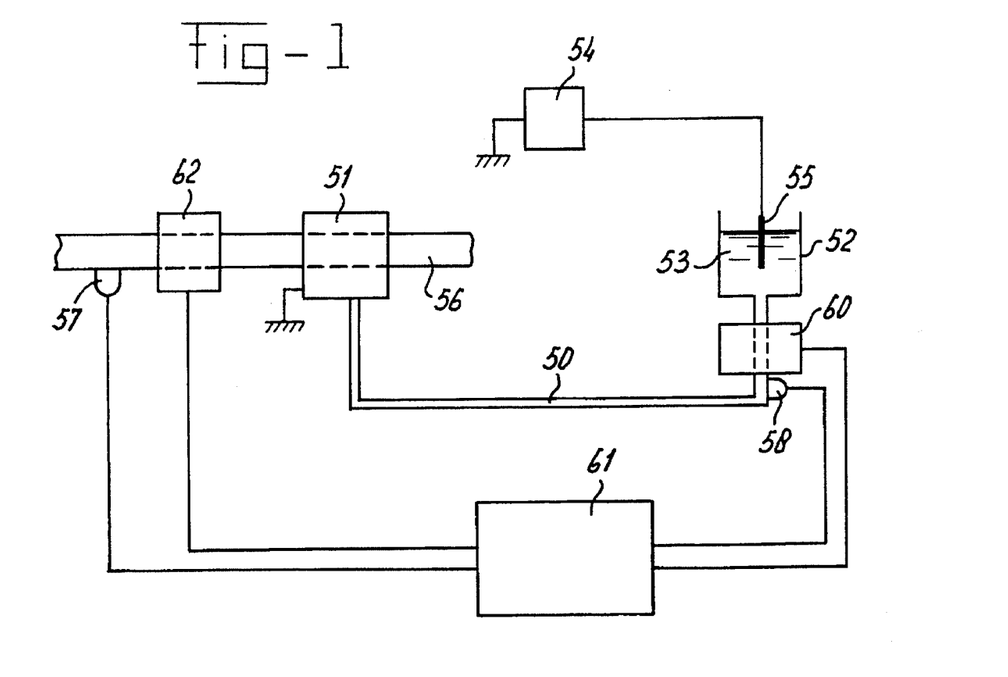
FIG. 1 illustrates schematically a system according to the invention.

FIG. 1 illustrates schematically a system according to the invention. The system comprises a capillary tube 50 extending between an input device 51 connected to the input opening of the capillary tube 50 and a reservoir 52 connected to the output opening of the capillary tube 50. The tube 50 is filled with an electrolyte 53. During operation a voltage gradient is developed within the capillary tube 50 by means of the voltage source 54. The high voltage output of the voltage source 54 is connected to an electrode 55 positioned within the electrolyte 53 in the reservoir 52. The other terminal of the voltage source 54 is earthed and also the input device 51 and therewith the input opening of the capillary tube 50 is connected to earth.

Figure 4A:
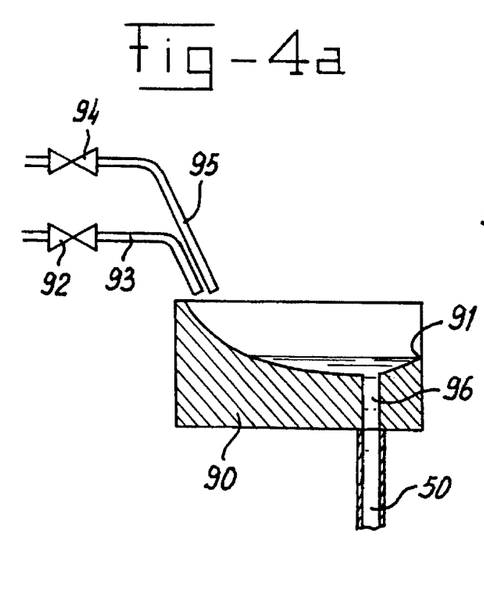
FIGS. 4a and 4b illustrate a preferred embodiment of an input device for injecting a sample in the input opening of the capillary tube.
Figure 4B:
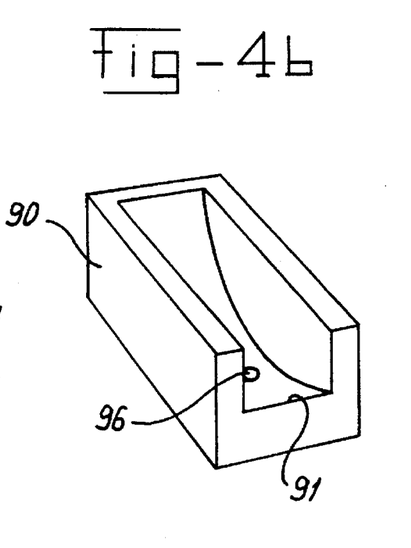

It is assumed that the solution to be analyzed flows through a tube 56. By means of the input device 51 a sample of the solution can be injected in the input opening of the capillary tube 50. A specific embodiment of said input device 51 will be described in more detail with reference to FIG. 4.

The system comprises furthermore a conductivity detector 60 which is attached to the detection area of the capillary tube 50. By means of this detector 80 the changes of the electrical conductivity of the electrolyte, caused by the passing ions of various types, is measured continuously. The detector 60 generates an electrical signal which is delivered to a processor 61. In agreement with the invention, the system comprises a second conductivity detector 62 for measuring the electrical conductivity of the solution to be analyzed, which solution flows through the channel 56. The signals generated by the second electrical conductivity detector 62 are also delivered to the processor 61.

A temperature sensor 58 is attached to the capillary tube, preferably directly adjacent to the detector 60, to provide a data signal to the processor 61 which is representative for the local temperature of the electrolyte and the ions therein. A further temperature sensor 57 is attached to the conduit 56 to provide a data signal to the processor 61 representative for the temperature of the solution flowing through the tube 56.

During operation, a sample of the solution in the channel 56 is injected by the input device 51 into the input opening of the capillary tube 50. Because the input opening of the capillary tube 50 is connected to earth and the output side thereof is, through the electrode 55, connected to a relatively high voltage, there is a voltage gradient in the electrolyte in the capillary tube which causes a migration of the ions injected by the input device 51 into the input opening of the capillary tube 50. Because the mobility of the various types of ions is different the ions will be separated into zones, the faster ions ahead followed by the more slower ions, and the passing of these zones of ions through the detection area is measured by the electrical conductivity detector 60. The time, elapsed between the moment of injection and the moment at which the ions pass the detector 60 is indicative of the type of ions. The degree of change in electrical conductivity, measured by the detector 60, is indicative of the concentration of the ions.

Figure 2:
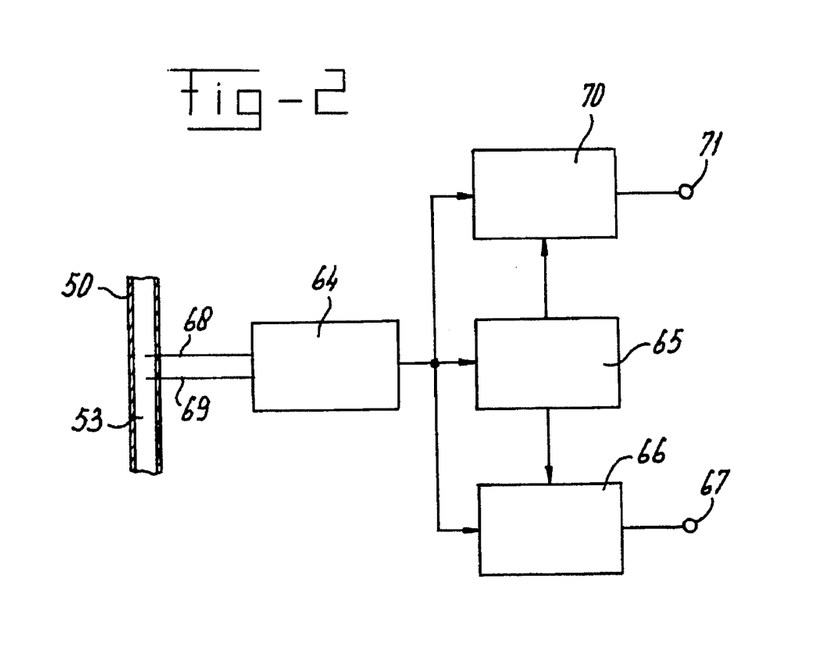
FIG. 2 illustrates a preferred embodiment of the detector circuit.
Figure 3:
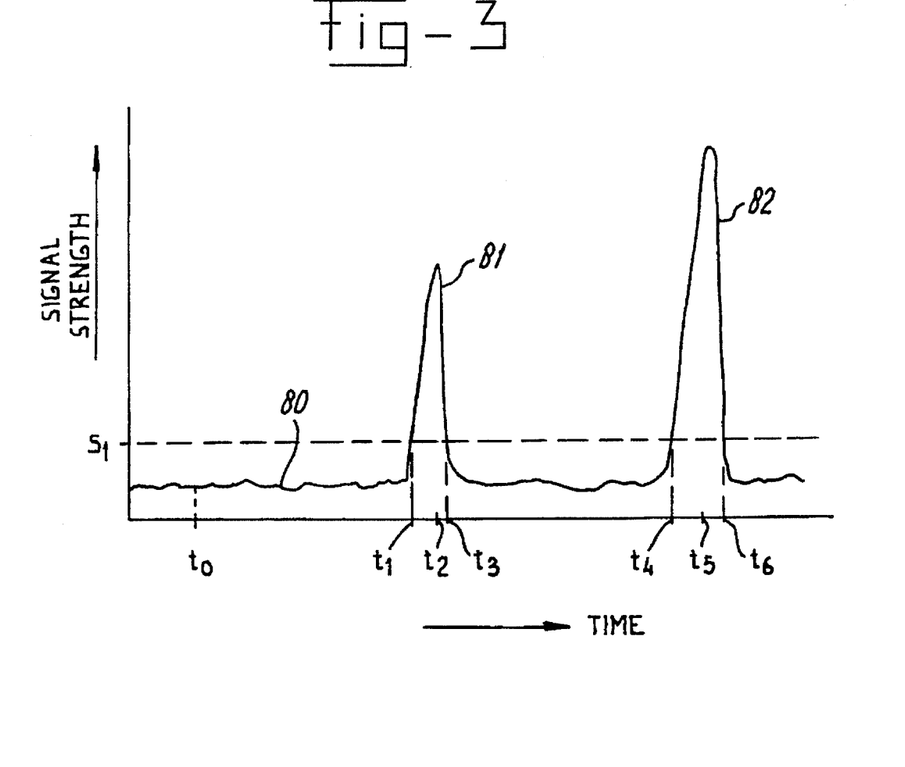
FIG. 3 illustrates the shape of the signal generated by the conductivity measurement circuit in the detector device according to FIG. 2.

A preferred embodiment of the detector circuit 60 is illustrated in FIG. 2. FIG. 2 shows a part of the capillary tube 50 filled with the electrolyte 53 in which the ions are migrating. The conductivity of the electrolyte is measured by two probes 68 and 69 connected to a conductivity measuring circuit 64. The signal generated at the output of the circuit 64 is schematically illustrated in FIG. 3. The generated signal is composed of a background signal 80 indicating the electrical conductivity of the electrolyte without ions, and a number of signal peaks, such as 81 and 82, indicating the presence of specific ions in the electrolyte. The output signal of the measuring circuit 64 is connected first of all to a level detector 65. The level detector 65 determines if the received signal is below or above a predetermined threshold level S1. The level S1 is well above the level of the background signal 80, but lover than the lowest expected peak signal. As soon as the level detector 65 detects a signal above the threshold level control signals are generated to activate an integrator 66 and a peak level detector 70, the functioning of which will be explained with reference to FIG. 3.

In FIG. 3 it is assumed that at time t0 a sample of the solution to be analyzed is in, acted by the input device 51 into the input opening of the capillary tube 50. Under the influence of the voltage gradient in the capillary tube the ions start migrating in the direction of the detector 60. As long as no ions will pass the detector 60 the signal generator by the detector 60 indicates only the background conductivity caused by the electrolyte. The corresponding signal 80 is underneath the threshold value S1 and under those circumstances the circuits 66 and 70 are not active. At moment t1 the level detector 65 detects a crossing of the level 31 and activates both the integrator 66 and the peak level detector 70. The integrator 66 integrates the signal at the output of the measuring circuit 64 from the moment t1 up to the moment t3 at which moment the level falls underneath the threshold level S1. Simultaneously, the peak level detector 70 detects the moment t2, at which moment the signal 81 reaches its maximum. Both the integrated value at the output terminal 67 as well as the time value at the terminal 71 are supplied to the processor 61 for further processing. At time t3 the level detector 65 will deactivate the circuits 66 and 70. At time t4 the whole process is repeated. The detector 65 detects a level crossing and activates the integrator 66 and the peak level detector 70 and at time t6 both circuits are deactivated again. The integrated value of the signal section 82 at the output 67 and the time at which the Signal 82 reaches its peak level at the output 71 are supplied to the processor 61 for further processing.

The processing of the received signals in the processor 61 is performed according to the following formula:

$$Y(t)*EC(t)=A\{[X1*Y1*EC(1)]+[X2*Y2*EC(2)]+\ldots\}$$

wherein:

EC(t)=the total electrical conductivity of the solution measured by the conductivity detector 62, EC(n)=the integrated conductivity value for ions of type n, received from the detector 60, Xn=factor dependent on the specific mobility of each type of ion, Yn=temperature dependent factor, Y(t)=temperature dependent factor of total solution, A=calibration factor.

The processor 61 cooperates with a number of memories or memory sections which are not separately illustrated in FIG. 1. In a first memory section the factors X1, X2, X3, . . . , dependent on the specific mobility of each different type of ion are stored. In a second memory section the factors Y1, Y2, Y3, . . . , relating to the temperature dependency of the various conductivity measurement values EC(1), EC(2), EC(3), . . . , are stored.

At the end of a complete measurement cycle, after all the various measurement values EC(n) are received both from the detector circuit 60 as well as from the detector circuit 62, the processor 61 retrieves, based on the temperature measurement values received from the detectors 57 and 58, for each specific ion a factor Xn and a factor Yn. Thereafter for each type of ion the term Xn*Yn*EC(n) is calculated, followed by a calculation of the sum of these various terms. Thereafter the calibration factor A is determined using the above-mentioned formula.

As soon as the calibration factor A is known, the concentration of the various types of ions can be calculated using the formula $$C(n) = \frac{Z(n)}{A} * EC(n)$$

wherein

C(n)=the concentration of ions of type n

Z(n)=a ion type dependent factor.

The processor 61 comprises a further memory section in which for each ion type a factor Z(n) is stored. For calculating the concentration of ions of type n, the factor Z(n) is retrieved from said memory section and the above-mentioned formula is applied to calculate C(n).

It will be clear to the expert in this field that the whole process can be performed completely automatically without any human assistance. A series of measurement cycles can be carried out if the input device 51 is embodied such that it can be controlled by the processor 61. As such, various remote controlled input devices are known. In general, these input devices are functioning with valve combinations, which after performing a sequence of opening and closing operations, inject a small sample of the solution to be analyzed into the input opening of the capillary tube. A disadvantage of these prior art devices is that the mechanical construction of these input devices is rather critical. Because of dimensional tolerances and leakage problems the actual volume of a sample is not accurately defined and not reproducible. The system according to the invention preferably comprises an input device which does not have these disadvantages.

A preferred embodiment of an input device 51 is schematically illustrated in FIG. 4. The device comprises a reservoir 90 which is open at the top and which has at its deepest level a bore through which fluid in the reservoir may flow into the capillary tube 50. The connection between the capillary tube 50 and the reservoir 90 can be made in any suitable manner and is not illustrated in detail. Because at one side the walls of the reservoir are relatively low, the reservoir will only hold a very small amount of fluid. Any further fluid added to the reservoir will flow over the edge 91. If the valve 92 is opened then clean electrolyte will flow through the conduit 93 into the reservoir. Any fluid present before will flow over the edge 91 so that, if the valve 92 is opening for a predetermined time, thereafter the reservoir will be filled only with clean electrolyte. If the valve 94 is opened the solution to be analyzed will flow through the tube 95 into the reservoir replacing the electrolyte which will flow over the edge 91. After opening the valve 94 for a predetermined time the reservoir 90 will only contain solution to be analyzed.

It will be clear that at the start of a measuring cycle the valve 94 is opened to fill the reservoir 90 with solution to be analyzed whereafter the valve 94 is closed. After a predetermined delay, long enough to be sure that sufficient ions are migrated through the bore 96 into the capillary tube 50, the valve 92 is opened to drain off the solution and to fill the reservoir 90 with clean electrolyte. It will be clear that in this manner a well defined sample of the solution to be analyzed is introduced into the capillary tube 50.

Preferably the reservoir 90 is made of a material which is electrically conducting and which does not interact chemically or in another way with the solution to be analyzed. A reservoir 90 made of an electrically conducting material has the advantage that the reservoir 90 can be used as the ground electrode for the voltage source 54. Because the input device 51 is in contact with the solution to be analyzed, also said solution and other parts of the tubing through which this solution flows are grounded enhancing thereby the security and safety of the system.

As already remarked above the system according to the invention is specifically suited for applications in which the solution to be analyzed contains a restricted number of different ions, which preferably are known as such. An application in the agricultural area will be described with reference to FIGS. 5–8.

Figure 5:
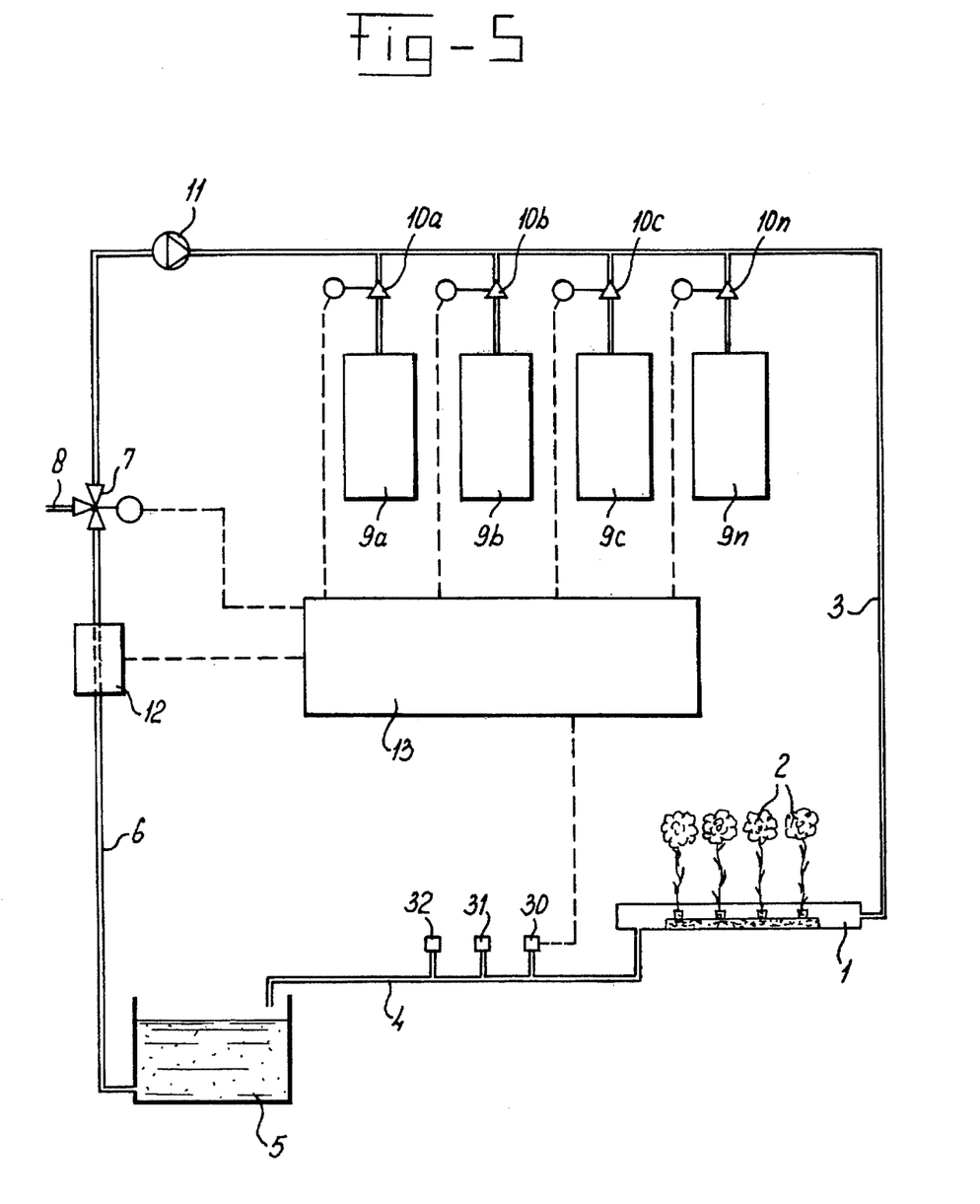
FIG. 5 illustrates schematically a system for growing plants, in which the ion concentrations are according to the invention measured by means of in ion detector functioning with capillary zone electrophoresis.

The system, which is schematically illustrated in FIG. 5, comprises one or more growing containers in which the plants 2 are grown. A nutrient solution is delivered to each growing container through a conduit 3. The drain water received from said growing containers is through a conduit 4 supplied to a reservoir 5. From the reservoir 5 the drain water is supplied through a conduit 6 to a valve 7, where the drain water eventually is mixed with clean water which, through conduit 8 is supplied to the valve 7. The resulting mixture passes thereafter successively a series of reservoirs 9a . . . 9n, each containing a predetermined nutrient. Through the valves 10a . . . 10n a selected amount of each nutrient can be added to the nutrient solution flowing through the conduit 3. The function of the pump 11 is to pump drain water from the reservoir 5 and to maintain a flow through the system of conduits. Eventually further pumps maybe present in the system.

The drain water in the conduit 4, received from the growing containers 1, can be watched with reference to temperature by means of a temperature measurement device 32, with reference to the acidity by means of the pH measuring device 31 and with reference to the electrical conductivity by means of the conductivity measurement device 30.

Besides the already mentioned components, the system comprises furthermore an ion analyzing apparatus 12 to which periodically samples of the nutrient solution from the conduit 6 are supplied. In this analyzing apparatus 12 the composition of the nutrient solution will be determined in a manner to be described in more detail. The analyzing apparatus 12 generates measurement signals, which are characteristic for the detected ion concentrations and which are delivered to a processor 13, which processes these signals, especially compares the signals with the desired ideal composition of the nutrient solution, and generates as a result thereof control signals for controlling the valves 7, 10a ... 10n, such that the nutrient solution which through conduit 3 is supplied to the growing containers 1 has the desired correct composition. Eventually signals from one or more of the measuring devices 30, 31 or 32 can be delivered to the processor 13. In FIG. 5 a schematic signal connected between the conductivity measuring device 30 and the processor 13 is illustrated.

Figure 6:
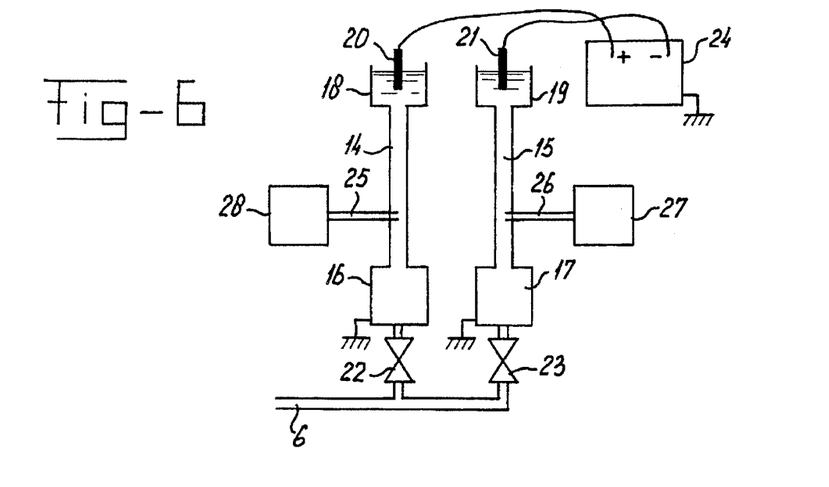
FIG. 6 illustrates in more detail an ion detector suitable for capillary zone electrophoresis.

The analyzing apparatus 12 comprises an ion detector functioning according to the capillary zone electrophoresis principle. An embodiment of such a detector is shown in FIG. 6. In this embodiment the detector comprises two capillary tubes 14 and 15 of which one end opens into an input chamber 16 respectively 17 and of which the other end opens into an electrode chamber 18 respectively 19, in which the electrodes 20 and 21 are installed. The input chambers 16 and 17 are through respective valves 22 and 23 connected to the sample conduit 6. The input chambers 16, 17, the capillary tubes 14, 15 and the electrode chambers 18 and 19 are filled with an electrically conducting electrolyte. Furthermore the detector comprises a voltage source 24 supplying a high positive voltage to the electrode 20 and a high negative voltage to the electrode 21. Furthermore the voltage source 24 is connected to earth just as the input chambers 16 and 17. The result thereof is that a voltage gradient is developed within the electrolyte in the capillary tubes 14 and 15.

In case by short operation of the valves 22 and 23 a drain water sample is entered from the conduit 6 into the input chambers 16 and 17, then the ions therein will start migrating as result of the voltage gradient in the capillary tubes 14 and 15. More specifically, the negative ions will start moving through the capillary tube 14 in the direction of the electrode 20 and the positive ions will start moving in the capillary tube 15 in the direction of the negative electrode 21. The velocity of movement of each of the ions is different for each type of ion. In each of the capillary tubes 14 and 15 a pair of detection electrodes 25 respectively 26 is installed for detecting the passage of a group of ions. Preferably for said detection a conductivity measurement is performed in which respect the electrodes 26 are schematically connected to a conductivity measuring device 27. The electrodes 25 are connected to a conductivity measuring device 28. The time period from the moment the sample was injected in the input chambers until the moment wherein a change in conductivity is detected between the detection electrodes is significant for the type of ions which at that moment pass the detection electrodes. The value of the conductivity change is a measure for the concentration of the respective ions.

Preferably the measurements are carried out simultaneously both for the positive ions as well as for the negative ions, so that for the measurements the same time scale can be used. In the embodiment of FIG. 6 it is therefore necessary to inject a sample of the nutrient solution simultaneously in both input chambers 16 and 17. To avoid eventual synchronization problems, which could arise during the injection step, it is preferred to use an embodiment of a capillary zone electrophoresis detector as is illustrated in FIG. 3. In FIG. 3 those components, which are not altered in comparison with FIG. 2, are indicated with the same reference numbers.

Figure 7:
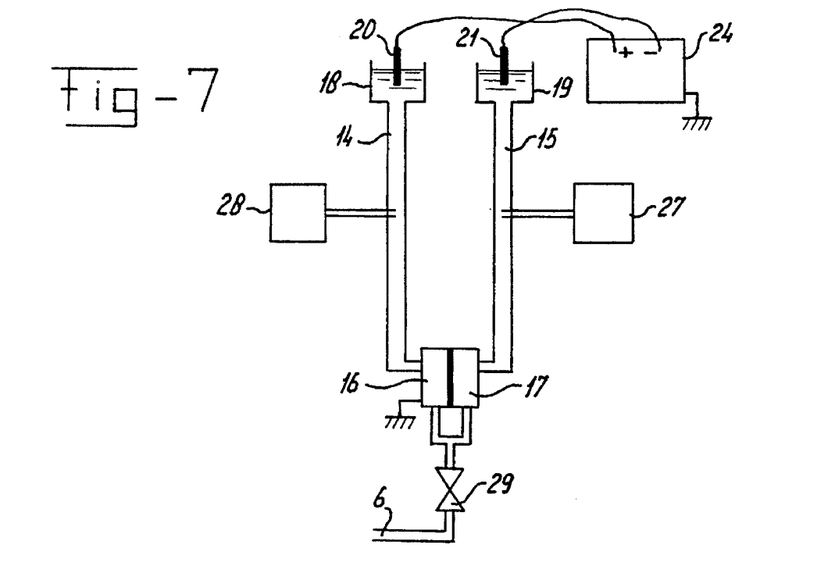
FIG. 7 illustrates a preferred embodiment of the detector suitable for capillary zone electrophoresis.

In the embodiment of the detector according to FIG. 7 both input chambers 16, 17 are connected to a common injection device 29. As soon as the samples are entered into the input chambers and the voltage source 24 is switched on, the positive ions will start migrating through the capillary tube 15 and the negative ions will start migrating through the capillary tube 14.

Figure 8:
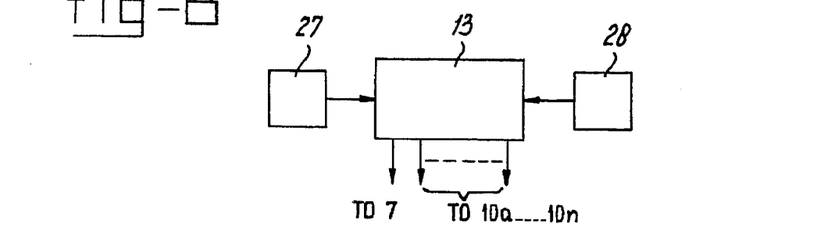

As is illustrated in FIG. 8 the signals, delivered by the conductivity measuring devices 27 and 28 will be supplied to a processor 13 in which, on the basis of a time period measurement and the corresponding conductivity measurement the type and concentration of the ions is determined. At the end of the measuring period in the processor the data about all ions are available. Thereafter these data can be compared with the desired ideal composition of the nutrient solution of which the data are entered into the processor in advance. Starting with this comparison it is possible to determine if one or more nutrients or if clean water has to be added to the solution to obtain the ideal composition. In correspondence therewith control signals for the valves 7, 10a ... 10n, are generated in such a manner that the correct amount of the respective nutrients respectively water is added.

As already indicated above the measurement value of the conductivity measurement device 30 can be supplied also to the processor 13, so that it becomes possible to compare the sum of the measurement values derived from the ion detector 12 with the total conductivity of the solution providing thereby an additional control on the correct functioning of the ion detector 12.

Although in FIG. 5 the ion detector 12 is installed in the conduit 6 it will be clear for the expert in this field that the composition of the nutrient solution can be determined at other places in the circuit with help of eventual further detectors. Eventually it is possible to add a multiplexer circuit to the ion detector 12 so that the composition of the nutrient solution at a number of places within the circuit can be determined by deriving sequentially samples from different points in the circuit.

We claim:

1. System for analyzing the concentration of a number of different ions in a watery solution, using a capillary zone electrophoresis apparatus comprising:

at least one capillary tube extending between an input opening and a detection area and filled with an electrolyte, an input device for injecting a sample of the solution to be analyzed in the input opening of the capillary tube, a voltage source for establishing a voltage gradient along the capillary tube between the input opening and the detection area to evoke a migration of the ions in said sample through the capillary tube, a detector circuit for detecting the ions passing through the capillary tube by measuring the conductivity of the passing fluid, a processor receiving data from said detector circuit representing momentary peak levels in the measured conductivity as well as moments in time at which the respective peaks appear, a further conductivity sensor providing to said processor data representing the total conductivity of the solution from which the sample was taken, said processor being programmed to determine for each detected peak in the measured conductivity level, the kind of ion and the concentration of the respective ion based on the data received from said detector circuit, and means for calculating the total conductivity, and means for comparing the calculated total conductivity with the total conductivity data provided by said further conductivity sensor to calibrate calculation parameters such that both the measured total conductivity and the calculated total conductivity will be equal.

2. System according to claim 1, wherein the input device comprises switching means for switching the input device between a first condition in which clean electrolyte is supplied to the input opening of the capillary tube and a second condition in which the solution to be analyzed is supplied to the input opening of the capillary tube, said switching means being connected to the processor to be controlled thereby.

3. System according to claim 1, wherein the system comprises two capillary tubes, a first one for the positive ions and a second one for the negative ions, each of said capillary tubes being connected to said input device and each extending between said input device and a respective first and second detection area, a first detection circuit being installed in the first detection area to detect the passage of the positive ions and a second detection circuit being installed in the second detection area to detect the passage of the negative ions, both detector circuits being connected to said processor to simultaneously supply measurement signals, and said voltage source including means for developing a voltage gradient of the one polar in the first capillary tube and a voltage gradient of the other polar in the second capillary tube.

4. System according to claim 3, wherein each detector circuit comprises a level detector which passes only signals above a predetermined level, and an integrator for integrating the output of the level detector.

5. System according to claim 1, wherein the processor cooperates with a first memory comprising for each type of ion to be analyzed the specific mobility dependent factor.

6. System according to claim 5, wherein the processor cooperates with a second memory comprising for each type of ion to be analyzed correction factors which are related to the temperature dependency of the electrical conductivity contribution of each ion type and of the electrical conductivity of the total solution.

7. System according to claim 6, wherein the processor cooperates with a third memory comprising for each type of ion to be analyzed an ion type dependent factor.

8. System according to claim 1, wherein said means for calculating the total conductivity include means for adding the conductivity contributions of each separate ion type to obtain a sum value which is compared with the measured total conductivity, and in case of a difference, said calculating means generating a correction factor such that after multiplying the contribution of the various separate ions with said correction factor and recalculating the total conductivity, said recalculated value equals the measured total conductivity.

9. System according to claim 8, wherein the conductivity contribution of each separate ion type is calculated with means for multiplying the measured conductivity value with a factor derived from the first memory section and a factor derived from the second memory section.

10. System according to claim 8, wherein the concentration of each ion type is calculated with means for multiplying the measured electrical conductivity contribution of each respective ion type with an ion type dependent factor, stored in said third memory, and means for dividing the result by said correction factor.

11. System according to claim 1, wherein the input device comprises a flow-through reservoir having a bottom which comprises an opening aligned with and connected to the input opening of the capillary tube, a solution input channel with a first remote controlled valve for supplying the solution to be analyzed, an electrolyte input channel with a second remote controlled valve for supplying clean electrolyte, and a drain channel for draining the contents of the reservoir, whereby during operation both said valves are controlled by the processor such that at the beginning of a measurement cycle, the first valve is opened for a predetermined period to deliver the solution to the reservoir and therewith to the input opening of the capillary tube, and that at the end of said predetermined period, the first valve is closed and the second valve is opened during a second predetermined period.

12. System according to claim 11, wherein the flow-through reservoir is made of an electrically conducting and chemically inert material.

13. System according to claim 11, wherein the voltage source is connected to the input device and to the detection area such that the input device is electrically at ground level.

* * * * *